United States Patent [19]

Heerze et al.

[11] Patent Number: 6,107,282

[45] Date of Patent: Aug. 22, 2000

[54] **TREATMENT OF *C. DIFFICILE* TOXIN B ASSOCIATED CONDITIONS**

[75] Inventors: Louis D. Heerze; Glen D. Armstrong, both of Edmonton, Canada

[73] Assignee: SYNSORB Biotech, Inc., Calgary, Canada

[21] Appl. No.: 09/419,790

[22] Filed: Oct. 18, 1999

Related U.S. Application Data

[63] Continuation of application No. 09/085,032, May 28, 1998, Pat. No. 6,013,635.

[51] Int. Cl.$^7$ ..................................................... A61K 31/70
[52] U.S. Cl. ............................................. 514/25; 536/17.9
[58] Field of Search ............................... 536/17.9; 514/25

[56] References Cited

U.S. PATENT DOCUMENTS

| | | | |
|---|---|---|---|
| 4,137,401 | 1/1979 | Lemieux et al. | 536/116 |
| 4,238,473 | 12/1980 | Lemieux et al. | 424/11 |
| 4,362,720 | 12/1982 | Lemieux et al. | 424/180 |
| 5,079,353 | 1/1992 | Ratcliffe et al. | 536/53 |
| 5,484,773 | 1/1996 | Heerze et al. | 514/23 |
| 5,635,606 | 6/1997 | Heerze et al. | 530/412 |
| 5,637,576 | 6/1997 | Heerze et al. | 514/61 |
| 5,767,093 | 6/1998 | Good et al. | 514/25 |
| 5,817,633 | 10/1998 | Heerze et al. | 514/23 |

OTHER PUBLICATIONS

Abbas, S.A., et al., "Tumor–Associated Oligosaccharide I: Synthesis of Sialyl–Lewis$^a$ Antigenic Determinant", *Sialic Acids*, Proc Japan–German Symp Berlin, 22–23 (1988).

Amvam–Zollo, P., et al., "*Streptococcus pneumoniae* Type XIV Polysaccharide: Synthesis of a Repeating Branched Tetrasaccharide with Dioxa–Type Spacer–Arms", *Carbohy Res*, 150:199–212 (1986).

Armstrong, G.D., et al., "Investigation of shiga–like toxin binding to chemically synthesized oligosaccharide sequences", *J Infect Dis*, 164:1160–7 (1991).

Barbut, F., et al., "Comparison of Enterotoxin Production, cytotoxin production, serogrouping and antimicrobial susceptibilities of *clostridium difficile* strains isolated from AIDS and human immunodeficiency virus–negative patients", *J Clin Microb*, 31:740–2 (1993).

Bartlett, J.D., "Treatment of antibiotic–associated pseudomembranous colitis", *Rev Infect Dis*, 6(Suppl 1): S235–41 (1984).

Bartlett, J.G., et al., "Antibiotic–associated pseudomembranous colitis due to toxin–producing clostridia", *N Engl J Med*, 298:531–534 (1978).

Bartlett J.G., "*Clostridium difficile:* History of its role as an enteric pathogen and the current state of knowledge about the organism", *Clin Infect Dis*, 18(Suppl 4):S265–272 (1994).

Bartlett, J.G., et al., "Symptomatic relapse after oral vancomycin therapy of antibiotic–associated pseudomembranous colitis", *Gastroent*, 78:431–4 (1989).

Chang, T.W., et al., "Inhibition of binding of *Clostridium difficile* toxin by steroids", *J Infect Dis*, 142:113 (1980).

Chernyak, A.Y., et al., "A New Type of Carbohydrate–Containing Synthetic Antigen: Synthesis of Carbohydrate–Containing Polyacrylamide Copolymers having the Specificity of 0:3 and 0:4 Factors of Salmonella", *Carbohy Res*, 128:269–282 (1984).

Clark, G.F., et al., "Toxin A from *Clostridium difficile* binds to rabbit erythrocyte glycolipids with terminal αGal(1–3)βGal(1–4)βGlcNAc sequences", *Arch Biochem Biophys*, 257:217–29 (1987).

Cox, D., et al. "A New Synthesis of 4–0–α–D–Galactopyranosyl–D–Galacto–Pyranose", *Carbohy Res*, 62:245–252 (1978).

Cozart, J.C., et al., "*Clostridium difficile* diarrhea in patients with AIDS versus non–AIDS controls. Method of treatment and clinical response to treatment", *J Clin Gastroent*, 16:192–4 (1993).

Dhamén, J., et al., "2–Bromoethyl glycosides: applications in the synthesis of spacer–arm glycosides," *Carbohy Res*, 118:292–301 (1983).

Dahmén, J., et al., "Synthesis of space arm, lipid, and ethyl glycosides of the trisaccharide portion [α–D–Gal–(1–4)–β–D–Gal(1–4)–β–D–Glc] of the blood group p$^k$ antigen: preparation of neoglycoproteins", *Carbohy Res*, 127:15–25 (1984).

Donta, S.T., et al., "Differential effects of *Clostridium difficile* toxins on tissue–cultured cells," *J Clin Microb*, 15:1157–1158 (1982).

Ekborg, G., et al., "Synthesis of Three Disaaccharides for the Preparation of Immunogens bearing Immunodeterminants Known to Occur on Glycoproteins", *Carbohy Res*, 110:55–67 (1982).

Fernandez–Santana, V., et al., "Glycosides of Monoallyl Diethylene Glycol. A New type of Spacer group for Synthetic Oligosaccharide", *J Carbohy Chem*, 8(3):531–537 (1989).

Finegold, S.M., et al., "Therapy directed against *Clostridium difficile* and its toxins. Complications of therapy". In Rolfe, R.D.,etal., (eds) *C. difficile:* It's Role in Intestinal Disease, Academic Press, Inc, San Diego, CA, 341–57 (1988).

Fiorentini, C., et al., "*Clostridium difficile* toxin A and its effect on cells," *Toxicon*, 29:543–567 (1991).

Flegel, W.A., et al., "Cytokine response by human monocytes to *Clostridium difficile* toxin A and toxin B," *Infect Immun*, 59:3659–3666 (1991).

(List continued on next page.)

Primary Examiner—Kathleen K. Fonda
Attorney, Agent, or Firm—Burns, Doane, Swecker & Mathis, LLP

[57] ABSTRACT

This invention relates to prevention and/or treatment of antibiotic associated diarrhea, including *Clostridium difficile* associated diarrhea (CDAD), pseudomembranous colitis (PMC) and other conditions associated with *C. difficile* infection, using oligosaccharide compositions which bind *C. difficile* toxin B. More specifically, the invention concerns neutralization of *C. difficile* toxin B associated with such conditions.

8 Claims, 2 Drawing Sheets

OTHER PUBLICATIONS

Fügedi, P., et al., "Thioglycosides as Glycosylating Agents in Oligosaccharide Synthesis", *Glycoconjugate J,* 4:97–108 (1987).

Garegg, P.J., et al., "A Synthesis of 8–Methoxycarbonyloct–1–yl O–β–D–Galactopyranosyl–(1→3)–0–β–D–Galactopyranosyl–(1→4)–2–Acetamido–2–Deoxy–β–D–Glucopyranoside", *Carbohy Res,* 136:207–213 (1985).

Garegg, P. J., et al., "Synthesis of 6– and 6' –deoxy derivatives of methyl 4–0–α–D–galactopyranosyl–β–D–galactopyranoside for studies of inhibition of pyelonephritogenic fimbriated *E. coli* adhesion to urinary epithelium–cell surfaces", *Carbohy Res,* 137:270–275 (1985).

Heerze, L.D., et al., "Oligosaccharide sequences attached to an inert support (SYNSORB) as potential therapy for antibiotic–associated diarrhea and pseudomembranous colitis," *J Infect Dis,* 169:1291–1296 (1994).

Jacquinet, J.C., et al., "Synthesis of Blood–group Substances, Part 11. Synthesis of the Trisaccharide O–α–D–Galactopyranosyl–(1→3)–0–β–D–galactopyranosyl–(1→4)–2–acetamido–2–deoxy–D–glucopyranose", *J C S Perkin,* 1:326–330 (1981).

Kameyama, A., et al., "Total synthesis of sialyl Lewis X", *Carbohy Res,* 209:c1–c4 (1991).

Kamiya, S., et al., "Analysis of purity of *Clostridium difficile* toxin A derived by affinity chromatography on immobilized bovine thyroglobulin", *FEMS Microb Lett,* 56:331–6 (1988).

Keighley, M.R.B., "Antibiotic–associated pseudomembranous colitis: pathogenesis and management", *Drugs,* 20:449–56 (1980).

Koike, K., et al., "Total Synthesis of Globotriaosyl–E and Z–Ceramides and Isoglobotriaosyl–E–Ceramide," *Carbohy Res,* 163:189–208 (1987).

Krivan, H.C., et al., "Cell surface binding site for *Clostridium difficile* enterotoxin: evidence for a glycoconjugate containing the sequence αGal(1–3)βGal(1–4)βGlcNAc", *Infect Immun,* 53:573–81 (1986).

Krivan, H.C., et al., "Purification of *Clostridium difficile* toxin A by affinity chromatography on immobilized bovine thyroglobulin", *Infect Immun,* 55:1873–7 (1987).

Lee, R.T., et al., "Synthesis of 3–(2–Aminoethylthio) PropylGlycosides", *Carbohy Res,* 37: 193–201 (1974).

Lemieux, R.U., et al., "The properties of a 'synthetic' antigen related to the blood–group Lewis A", *J Am Chem Soc,* 97:4076–83 (1975).

Lima, A.A., et al., "Effects of *Clostridium difficile* toxins A and B in rabbit small and large intestine in vivo and on cultured cells in vitro," *Infect Immun,* 56:582–588 (1988).

Lyerly, D.M., et al., "Effects of *Clostridium difficile* toxins given intragastrically to animals," *Infect Immun,* 47:349–352 (1985).

Lyerly, D.M., et al., "*Clostridium difficile:* Its disease and toxins", *Clin Microb Rev,* 1:1–18 (1988).

Lyerly, D.M., "Epidemiology of *Clostridium difficile* disease", *Clin Microb News,* 15:49–53 (1993).

Okamoto, K., et al., "Glycosidation of Sialic Acid," *Tetrahedron,* 47:5835–5857 (1990).

Onderdonk, A.B., et al., "Comparative effects of clindamycin and clindamycin metabolites in the hamster model for antibiotic–associated colitis", *J Antimicrob Chem,* 8:383–93 (1981).

Paulsen, "Advances in Selective Chemical Syntheses of Complex Oligosaccharide", *Angew Chem Int Ed Eng,* 21:155–173 (1982).

Paulsen, H., "Syntheses von oligosaccharide–determinanten mit amid–spacer vom typ des T–antigens", *Carbohy Res,* 104:195–219 (1982).

Rana, S.S., et al., "Synthesis of Phenyl 2–Acetamido–2–Deoxy–3–O–α L–Fucopyranosyl–β–D–Glucopyranoside and Related Compounds", *Carbohy Res,* 91:149–157 (1981).

Riegler, M., et al., *J Clin Invest,* 95:2004–2011 (1995).

Rolfe, R.D., "Binding kinetics of *Clostridium difficile* toxin A and B to intestinal brush border membranes from infant and adult hamsters," *Infect Immun,* 59:1223–1230 (1991).

Schaubach, R., et al., "Tumor–Associated Antigen Synthesis: Synthesis of the Gal–α–(1→3)–Gal–β–(1→4)–GlCNAc Epitope. A specific Determinant for Metastatic Progression?," *Liebigs Ann Chem,* 607–614 (1991).

Schmidt, "New Methods for the Synthesis of Glycosides and Oligosaccharide—Are There Alternatives to the Koenigs–Knorr Method?" *Angew Chem Int Ed Eng,* 25:212–235 (1986).

Smith, D.J., et al., "Purification and antigenicity of a novel glucan–binding protein of Streptococcus mutans," *Infect Immun,* 62:2545–2552 (1994).

Sullivan, N.M., et al., "Purification and characterization of toxin A and B from *Clostridium difficile*", *Infect Immun,* 35:1032–40 (1983).

Tedesco, F.J., "Pseudomembranous colitis: Pathogenesis and therapy", *Med Clin No Am,* 66:655–64 (1982).

Torres, J., et al., "Enterotoxins from *Clostridium difficile;* Diarrhoeogenic potency and morphological effects in the rat intestine," *Gut,* 31:781–785 (1990).

Triadafilopoulos, G., et al., "Differential effects of *Clostridium difficile* toxins A and B on rabbit ileum," *Gastroent,* 93:273–279 (1987).

Tucker, K.D., et al., "Toxin A of *Clostridium difficile* binds to carbohydrate antigens I, X, and Y", *Infect Immun,* 59:73–8 (1991).

Von Eichel–Streiber, C., et al., "*Clostridium difficile* toxin A carries a c–terminal repetitive structure homologous to the carbohydrate binding region of streptococcal glycosyltransferases", *Gene,* 96:107–13 (1990).

Von Eichel–Streiber, C., et al., "Comparative sequence analysis of the *Clostridium difficile* toxins A and B", *Mol Gen Genet,* 233:260–268 (1992).

Wren, B.W., et al., "Antigenic cross–reactivity and functional inhibition by antibodies to *Clostridium difficile* toxin A, Streptococcus mutans glucan–binding protein, and a synthetic peptide", *Infect Immun,* 59:3151–5 (1991).

Wren, B.W., "A family of clostridial and streptococcal ligand–binding proteins with conserved C–terminal repeat sequences", *Mol Microb,* 5:797–803 (1991).

FIG. 2A

Percent Toxin B Neutralization (n=2)
- SYN 179A (isomaltose)
- SYN Cd
- SYN 5-174
- SYN ASA

FIG. 2B

Percent Toxin A Neutralization (n=2)
- SYN 179A (isomaltose)
- SYN Cd
- SYN 5-174

TREATMENT OF C. DIFFICILE TOXIN B ASSOCIATED CONDITIONS

This application is a continuation of application Ser. No. 09/085,032, filed May 28, 1998 now U.S. Pat. No. 6,013,635.

FIELD OF THE INVENTION

This invention relates to treatment of antibiotic associated diarrhea, including Clostridium difficile associated diarrhea (CDAD) and pseudomembranous colitis (PMC) and other conditions associated with C. difficile infection. More specifically, the invention concerns neutralization of C. difficile toxin B, a cytotoxin associated with CDAD, PMC and other conditions caused by C. difficile.

REFERENCES

The following references are cited in the application as numbers in brackets ([]) at the relevant portion of the application.

1. Bartlett, J. G., et al., "Antibiotic-associated pseudomembranous colitis due to toxin-producing clostridia", N. Engl. J. Med., 298:531–534 (1978).

2. Lyerly, D. M., "Epidemiology of Clostridium difficile disease", Clin. Microbiol. News, 15:49–53 (1993).

3. Cozart, J. C., et al., "Clostridium difficile diarrhea in patients with AIDS versus non-AIDS controls. Method of treatment and clinical response to treatment", J. Clin. GastroenteroL, 16:19–24 (1993).

4. Barbut, F., et al., "Comparison of Enterotoxin Production, cytotoxin production, serogrouping and antimicrobial susceptibilities of Clostridium difficile strains isolated from AIDS and human immunodeficiency virus-negative patients", J. Clin. Microbiol., 31:740–2 (1993).

5. Krivan, H. C., et al., "Cell surface binding site for Clostridium difficile enterotoxin: evidence for a glycoconjugate containing the sequence $\alpha$Gal(1-3)$\beta$Gal(1–4)$\beta$GlcNAc", Infect Immun., 53:573-81(1986).

6. Clark, G. F., et al., "Toxin A from Clostridium difficile binds to rabbit erythrocyte glycolipids with terminal $\alpha$Gal(1-3)$\beta$Gal(1–4)$\beta$GlcNAc sequences", Arch. Biochem. Biophys., 257:217–29 (1987).

7. Tucker, K. D., et al., "Toxin A of Clostridium difficile binds to carbohydrate antigens I, X, and Y", Infect. Immun., 59:73–8 (1991).

8. Krivan, H. C., et al., "Purification of Clostridium difficile toxin A by affinity chromatography on immobilized bovine thyroglobulin", Infect. Immun., 55:1873–7 (1987).

9. Kamiya, S., et al., "Analysis of purity of Clostridium difficile toxin A derived by affinity chromatography on immobilized bovine thyroglobulin", FEMS Microbiol. Lett., 56:331–6 (1988).

10. Armstrong, G. D., et al., "Investigation of shiga-like toxin binding to chemically synthesized oligosaccharide sequences", J. Infect. Dis., 164:1160–7 (1991).

11. Von Eichel-Streiber, C., et al., "*Clostridium difficile* toxin A carries a c-terminal repetitive structure homologous to the carbohydrate binding region of streptococcal glycosyltransferases", Gene, 96:107–13 (1990).

12. Lemieux, R. U., et al., "The properties of a 'synthetic' antigen related to the blood-group Lewis A", *J. Am. Chem. Soc.,* 97:4076–83 (1975).

13. Sullivan, N. M., et al., "Purification and characterization of toxin A and B from *Clostridium difficile", Infect. Immun.,* 35:1032–40 (1983).

14. Finegold, S. M., et al., "Therapy directed against *Clostridium difficile* and its toxins. Complications of therapy". In Rolfe, R.D.,et al., (eds) C. difficile: It's Role in Intestinal Disease, Academic Press, Inc., San Diego, Calif., 341–57 (1988).

15. Bartlett, J. G., et al., "Symptomatic relapse after oral vancomycin therapy of antibiotic-associated pseudomembranous colitis", *Gastroenterology,* 78:431–4 (1989).

16. Tedesco, F. J., "Pseudomembranous colitis: Pathogenesis and therapy", *Med. Clin. North Am.,* 66:655–64 (1982).

17. Keighley, M. R. B., "Antibiotic-associated pseudomembranous colitis: pathogenesis and management", *Drugs,* 20:449–56 (1980).

18. Bartlett, J. D., "Treatment of antibiotic-associated pseudomembranous colitis", *Rev. Infect. Dis.,* 6, Suppl. 1:1–55 (1984).

19. Onderdonk, A. B., et al., "Comparative effects of clindamycin and clindamycin metabolites in the hamster model for antibiotic-associated colitis", *J. Antimicrob. Chem.,* 8:383–93 (1981).

20. Triadfilopoulos, G., et al., "Differential effects of *Clostridium difficile* toxin a and b on rabbit ileum", *Gastroenterology,* 93:273–9 (1987).

21. Lemieux, R. U., et al., "Glycoside-Ether-Ester Compounds", U.S. Pat. No. 4,137,401, issued Jan. 30, 1979.

22. Lemieux, R. U., et al., "Artificial Oligosaccharide Antigenic Determinants", U.S. Pat. No. 4,238,473, issued Dec. 9, 1980.

23. Lemieux, R. U., et al., "Synthesis of 2-Amino-2-Deoxyglycoses and 2-Amino-2-Deoxyglycosides from glycals", U.S. Pat. No. 4,362,720, issued Dec. 7, 1982.

24. Cox, D., et al. "A New Synthesis of 4-0-α-D-Galactopyranosyl-D-Galacto-Pyranose", *Carbohy. Res.,* 62: 245–252 (1978).

25. Dahmen, J., et al., "Synthesis of space arm, lipid, and ethyl glycosides of the trisaccharide portion [α-D-Gal-(1–4)-β-D-Gal(1–4)-β-D-Glc] of the blood group $p^k$ antigen: preparation of neoglycoproteins", *Carbohy. Res.,* 127:15–25 (1984).

26. Garegg, P. J., et al., "A Synthesis of 8-Methoxycarbonyloct-1-yl O-α-D-Galactopyranosyl-(1→3)-0-β-D-Galactopyranosyl-(1-→4)-2-Acetamido-2-Deoxy-β-D-Glucopyranoside", *Carbohy. Res.,* 136: 207–213 (1985).

27. Garegg, P. J., et al., "Synthesis of 6- and 6'-deoxy derivatives of methyl 4-0-α-D-galactopyranosyl-β-D-galactopyranoside for studies of inhibition of pyelonephritogenic fimbriated *E. coli* adhesion to urinary epithelium-cell surfaces", *Carbohy. Res.,* 137: 270–275 (1985).

28. Jacquinet, J. C., et al., "Synthesis of Blood-group Substances, Part 11. Synthesis of the Trisaccharide O-α-D-Galactopyranosyl-(1→3)-O-β-D-galactopyranosyl-(1→4)-2-acetamido-2-deoxy-D-glucopyranose", J. C. S. Perkin, 1:326–330 (1981).

29. Koike, K., et al., "Total Synthesis of Globotriaosyl-E and Z-Ceramides and lsoglobotriaosyl-E-Ceramide," *Carbohy. Res.,* 163: 189–208 (1987).

30. Schaubach, R., et al., "Tumor-Associated Antigen Synthesis: Synthesis of the Gal-α-(1→3)-Gal-β-(1→4)-GlCNAc Epitope. A specific Determinant for Metastatic Progression?," *Liebigs Ann. Chem.,* 607–614 (1991).

31. Ratcliffe, R. M., et al., "Sialic Acid Glycosides, Antigens, Immunoadsorbents, and Methods for Their Preparation", U.S. Pat. No. 5,079,353, issued Jan. 7,1992.

32. Okamoto, K., et al., "Glycosidation of Sialic Acid," *Tetrahedron*, 47: 5835–5857 (1990).

33. Abbas, S. A., et al., "Tumor-Associated Oligosaccharide 1: Synthesis of Sialyl-Lewis$^a$ Antigenic Determinant", *Sialic Acids*, Proc. Japan-German Symp. Berlin, 22–23 (1988).

34. Paulsen, "Advances in Selective Chemical Syntheses of Complex Oligosaccharide", *Angew. Chem. Int. Ed. Eng.*, 21:155–173 (1982).

35. Schmidt, "New Methods for the Synthesis of Glycosides and Oligosaccharide - Are There Alternatives to the Koenigs-Knorr Method?" *Angew. Chem. Int Ed. Eng.*, 25:212–235 (1986).

36. Fugedi, P., et al., "Thioglycosides as Glycosylating Agents in Oligosaccharide Synthesis", *Glycoconjugate J.*, 4:97–108 (1987).

37. Kameyama, A., et al., "Total synthesis of sialyl Lewis X", *Carbohy. Res.*, 209: c1–c4 (1991).

38. Ekborg, G., et al., "Synthesis of Three Disaccharides for the Preparation of Immunogens bearing Immunodeterminants Known to Occur on Glycoproteins", *Carbohy. Res.*, 110: 55–67 (1982).

39. Dahmen, J., et al., "2-Bromoethyl glycosides: applications in the synthesis of spacer-arm glycosides,"*Carbohy. Res.*, 118: 292–301 (1983).

40. Rana, S. S., et al., "Synthesis of Phenyl 2-Acetamido-2-Deoxy-3-O-αL-Fucopyranosyl-β-D-Glucopyranoside and Related Compounds", *Carbohy. Res.*, 91: 149–157 (1981).

41. Amvam-Zollo, P., et al., "Streptococcus pneumoniae Type XIV Polysaccharide: Synthesis of a Repeating Branched Tetrasaccharide with Dioxa-Type Spacer-Arms", *Carbohy. Res.*, 150:199–212 (1986).

42. Paulsen, H., "Synthese von oligosaccharid-determinanten mit amid-spacer vom typ des T-antigens", *Carbohy. Res.*, 104:195–219 (1982).

43. Chernyak, A. Y., et al., "A New Type of Carbohydrate-Containing Synthetic Antigen: Synthesis of Carbohydrate-Containing Polyacrylamide Copolymers having the Specificity of 0:3 and 0:4 Factors of Salmonella", *Carbohy. Res.*, 128: 269–282 (1984).

44. Fernandez-Santana, V., et al., "Glycosides of Monoallyl Diethylene Glycol. A New type of Spacer group for Synthetic Oligosaccharide", *J. Carbohy. Chem.*, 8(3), 531–537 (1989).

45. Lee, R. T., et al., "Synthesis of 3-(2-Aminoethylthio) PropylGlycosides", *Carbohy. Res.*, 37: 193–201 (1974).

46. Riegler, M., Sedivy, R., Pothoulakis, C., Hamilton, G., Zacherl, J., Bischof, G., Cosentini, E., Feil, W., Schiessel, R., LaMont, J. T., Wenzl, E., *J. Clin. Invest.*, 95:2004–2011 (1995).

47. Chang T. W., Gorbach, S. L., Bartlett, J. G., "Inhibition of binding of *Clostridium difficile* toxin by steroids", *J. Infect. Dis.*, 142:113 (1980).

48. Lyerly, D. M., Krivan, H. C., Wilkens, T. D., "*Clostridium difficile*: Its disease and toxins", *Clin. Microb. Rev.*, 1:1–18 (1988).

49. Wren, B. W., Russell, R. R. and Tabaqchali, S., "Antigenic cross-reactivity and functional inhibition by antibodies to *Clostridium difficile* toxin A, Streptococcus mutans glucan-binding protein, and a synthetic peptide", *Infect. Immun.*, 59:3151–5 (1991).

50. Wren, B. W., "A family of clostridial and streptococcal ligand-binding proteins with conserved C-terminal repeat sequences", *Mol. Microbiol,* 5:797–803 (1991).

51. von Eichel-Streiber, C., Laufenberg-Feldmann, R., Sartingen, S., Schulze, J., Sauerborn, M., "Comparative sequence analysis of the *Clostridium difficile* toxins A and B", *Mol. Gen. Genet.*, 233:260–268 (1992).

52. Smith, D. J., Akita, H., King, W. F., Taubman, M. A., "Purification and antigenicity of a novel glucan-binding protein of Streptococcus mutans,"*Infect. Immun.*, 62:2545–2552 (1994).

53. Rolfe, R. D., "Binding kinetics of *Clostridium difficile* toxin A and B to intestinal brush border membranes from infant and adult hamsters,"*Infect Immun.*, 59:1223–1230 (1991).

54. Bartlett, J. G., "*Clostridium difficile*: history of its role as an enteric pathogen and the current state of knowledge about the organism", *Clin. Infect. Dis.*, 18 (Suppl 4):S265–272 (1994).

55. Bartlett, J. G., Chang, T. W., Gurwith, M., Gorbach, S. L., Onderdonk, A. B., "Antibiotic-associated *pseudomembranous colitis* due to toxin-producing clostridia," *N. Eng. J. Med.* , 298: 531–534 (1978).

56. Triadafilopoulos, G., Pothoulakis, C., O'Brien, M. J., LaMont, J. T., "Differential effects of *Clostridium difficile* toxins A and B on rabbit ileum," *Gastroenterology*, 93:273–279 (1987).

57. Lyerly, D. M., Saum, K. E., MacDonald, D. K., Wilkins, T. D., "Effects of *Clostridium difficile* toxins given intragastrically to animals," *Infect Immun.*, 47:349–352 (1985).

58. Torres, J., Jennische, E., Lange, S., Lonnroth, I., "Enterotoxins from *Clostridium difficile;* diarrhoeogenic potency and morphological effects in the rat intestine," *Gut*, 31:781–785 (1990).

59. Flegel, W. A., Muller, F., Daubener, W., Fischer, H. G., Hadding, U., Northoff, H., "Cytokine response by human monocytes to *Clostridium difficile* toxin A and toxin B," *Infect. Immun.*, 59:3659–3666 (1991).

60. Heerze, L. D., Kelm, M. A., Talbot, J. A., Armstrong, G. D., "Oligosaccharide sequences attached to an inert support (SYNSORB) as potential therapy for antibiotic-associated diarrhea and *pseudomembranous colitis,*" *J. Infect. Dis.*, 169:1291–1296 (1994).

61. Sullivan, N. M., Pellet, S. and Wilkins, T. D., "Purification and characterization of toxin A and B from *Clostridium difficile,*" *Infect Immun.*, 35:1032–1040 (1982).

62. Lima, A. A., Lyerly, D. M., Wilkins, T. D., lnnes, D. J., Guerrant, R. L., "Effects of *Clostridium difficile* toxins A and B in rabbit small and large intestine in vivo and on cultured cells in vitro," *Infect. Immun.*, 56:582–588 (1988).

63. Donta, S. T., Sullivan, N., Wilkins, T. D., "Differential effects of *Clostridium difficile* toxins on tissue-cultured cells," *J. Clin. Microb.*, 15:1157–1158 (1982).

64. Fiorentini, C., Thelestam, M., "*Clostridium difficile* toxin A and its effect on cells," *Toxicon*, 29:543–567 (1991).

65. Heerze, et al., U.S. Pat. No. 5,484,773 (1996).

66. Heerze, et al., U.S. Pat. No. 5,635,606 (1996).

67. Hinsgaul, O., et al., PCT/CA97/00862 (1997).

68. Hinsgaul, O., et al., PCT/CA97/00863 (1997).

69. Hinsgaul, O., et al., PCT/CA97/00864 (1997).

70. Hinsgaul, et al., PCT/CA97/00851 (1997).

The disclosure of the above publications, patents and patent applications are herein incorporated by reference in their entirety to the same extent as if the language of each individual publication, patent and patent application were specifically and individually included herein.

BACKGROUND OF THE INVENTION

The anaerobic organism *Clostridium difficile* is the major causative agent of antibiotic-associated bacterial diarrhea and pseudomembranous colitis (PMC) among mainly elderly patients in hospitals and long term care facilities [1,2]. The organism cannot compete successfully with the normal microbial flora in the adult colon, but when the normal intestinal microflora is altered, for example by antibiotic treatment, *C. difficile* is able to colonize the gut in high numbers. Antibiotic therapy accounts for 98% of all cases of *C. difficile* associated diarrhea (CDAD). However, any predisposing condition which alters the normal intestinal flora, including any condition which requires extensive immunosuppressive treatment, can also lead to the development of CDAD. For example, recent evidence suggests that AIDS patients are also high risk candidates for acquiring CDAD [3,4].

*C. difficile* produces two exotoxins, toxin A (an enterotoxin) and toxin B (a cytotoxin) which appear to play important roles in causing CDAD. It has long been thought that toxin A is primarily responsible for the disease. It acts by binding to epithelial cells in the intestine, resulting in the destruction of these cells and causing the secretion of fluid into the intestine. The destruction of these protective epithelial cells by toxin A represents the crucial step leading to the development of diarrhea. Once damage has occurred to the epithelial cells, the potent cytotoxin B can then gain access to underlying sensitive tissues and initiate additional clinical symptoms [–10,13,19–20,53–56,57–59,61–64]. However, in a recent in vitro study [46], toxin B was found to be more potent at damaging human colonic epithelium than toxin A, suggesting that toxin B may play a more important role in CDAD than previously believed.

Toxin A has been found to display a lectin-like activity which allows it to bind to an oligosaccharide receptor on epithelial cells. Several oligosaccharide sequences have been identified as potential receptors for toxin A [60,66]. The cellular receptor for toxin B has not been determined, but there are some indications that toxin B binds to erythrocytes implying that a carbohydrate receptor may be involved in toxin B binding [47, 48]. Steroids have also been proposed as potential receptors for toxin B [47].

The current therapy for patients who suffer from CDAD or PMC is to remove the offending drug and begin oral administration of the antibiotics Metronidazole or Vancomycin along with fluid replacement [3,14]. Vancomycin is only used in certain situations when patients cannot tolerate or are not responsive to Metronidazole treatment. Vancomycin is not used routinely because of its high cost and the possibility that its overuse may encourage the development of Vancomycin resistant microorganisms. Metronidazole therapy is effective in about 80% of the patients who suffer from CDAD or PMC. In about 20% of patients, the diarrhea returns after discontinuing antibiotic treatment [15]. In such individuals, episodes continue to recur until the normal intestinal flora is reestablished and the number of *C. difficile* organisms is reduced. This is a slow process, since antibiotics such as Metronidazole, which disturb the balance of the normal intestinal flora, are administered each time the diarrhea occurs.

The only other treatment for CDAD and PMC which removes toxin activity from the intestinal tract involves the use of multigram quantities of anion exchange resins such as cholestyramine and colestipol given orally in combination with antibiotics. This approach has been used to treat mild to moderately ill patients, as well as individuals who suffer from multiple episodes of diarrhea [16,17]. This form of therapy has only been moderately successful in treating the disease [18]. In addition to their lack of efficacy, there are several other disadvantages associated with the use of ion exchange resins. Ion exchange resins do not bind specifically to toxin A or toxin B. Thus, ion exchange resins may also bind antibiotics, resulting in suboptimal levels of antibiotic within the gut. This can also occur with other medications patients may be receiving for unrelated conditions. A further disadvantage of ion exchange resins is the disagreeable lingering taste which is associated with oral administration of these compounds.

With respect to methods of diagnosis, one method for detecting *C. difficile* in a sample is to culture the sample. The disadvantages of this method include the length of time required to obtain a result and interference by non-pathogenic, i.e. non-toxin producing, *C. difficile* strains. Other methods involve the use of specific antisera or monoclonal antibodies. These methods are based on the detection of toxin A or toxin B in clinical samples. U.S. Pats. Nos. 4,863,852 and 5,098,826 describe methods for detecting *C. difficile* toxin A by the use of reagents containing biological receptors for toxin A, including the $\alpha Gal(1-3)\beta Gal(1-4)\beta GlcNAc$, X and Y antigen oligosaccharide sequences, bound to a support. U.S. Pat. No. 5,635,606 teaches that certain synthetic oligosaccharide sequences covalently attached to a biocompatible solid support, e.g., Chromosorb p™, may be used to bind toxin A.

In view of the above, there is a need for an effective treatment for antibiotic associated diarrhea. In particular, a compound is needed which can neutralize *C. difficile* toxin B and/or both *C. difficile* toxin A and toxin B. A preferred compound would be administered noninvasively, such as orally, in a suitable pharmaceutical formulation.

SUMMARY OF THE INVENTION

The invention provides compositions and methods for the prevention and treatment of antibiotic associated diarrhea, pseudomembranous colitis and other conditions caused by *Clostridium difficile* toxin B.

In one aspect, the invention provides a method to bind and remove *C. difficile* toxin B from a sample suspected of containing said toxin B comprising contacting the sample with at least one toxin B binding oligosaccharide sequence covalently attached to an inert support through a non-peptidyl compatible linker arm under conditions wherein the toxin B is absorbed to the support; and separating the support containing the absorbed toxin B from the sample.

In another aspect, the invention provides a method to prevent or ameliorate one or more conditions mediated by *C. difficile* toxin B in a patient suffering from or susceptible to said condition, comprising administering to the patient an effective amount of a composition comprising at least one toxin B binding oligosaccharide sequence covalently attached to a pharmaceutically acceptable inert support through a non-peptidyl compatible linker arm, wherein said oligosaccharide sequence binds toxin B, and wherein the composition is capable of being eliminated from the gastrointestinal tract.

In a further aspect, the invention provides a pharmaceutical composition useful in treating or preventing CDAD and related conditions initiated by *C. difficile* toxin B, comprising at least one oligosaccharide sequence covalently attached to a pharmaceutically acceptable inert support through a non-peptidyl compatible linker arm, wherein said oligosaccharide sequence binds toxin B, and a pharmaceutically acceptable carrier, wherein said composition is capable of being eliminated from the gastrointestinal tract.

In yet another aspect, the invention provides a method to bind and remove C. difficile toxins A and B from a sample suspected of containing said toxins A and B comprising contacting the sample with at least one toxin A binding oligosaccharide sequence and at least one toxin B binding oligosaccharide sequence covalently attached to an inert support through a non-peptidyl compatible linker arm under conditions wherein the toxins are absorbed to the support; and separating the support containing the absorbed toxins from the sample.

In a still further aspect, the invention provides a method to prevent or ameliorate one or more conditions mediated by C. difficile toxins A and B in a patient suffering from or susceptible to said condition, comprising administering to the patient an effective amount of a composition comprising at least one toxin A binding oligosaccharide sequence and at least one toxin B binding oligosaccharide sequence covalently attached to a pharmaceutically acceptable inert support through a non-peptidyl compatible linker arm, wherein said oligosaccharide sequences bind toxins A and B, and wherein the composition is capable of being eliminated from the gastrointestinal tract.

In a yet further aspect, the invention provides a pharmaceutical composition useful in treating or preventing CDAD and related conditions initiated by C. difficile toxins A and B, comprising at least one oligosaccharide sequence covalently attached to a pharmaceutically acceptable inert support through a non-peptidyl compatible linker arm, wherein said oligosaccharide sequence(s) binds both toxin A and toxin B, and a pharmaceutically acceptable carrier, wherein said composition is capable of being eliminated from the gastrointestinal tract.

BRIEF DESCRIPTION OF THE DRAWINGS

FIG. 2 illustrates that SYNSORB 5174, which has both the Cd and the isomaltose oligosaccharide covalently bound by their respective linkers, neutralized both toxin A and B activity.

DETAILED DESCRIPTION OF THE INVENTION

A. Definitions

Figure 1A:
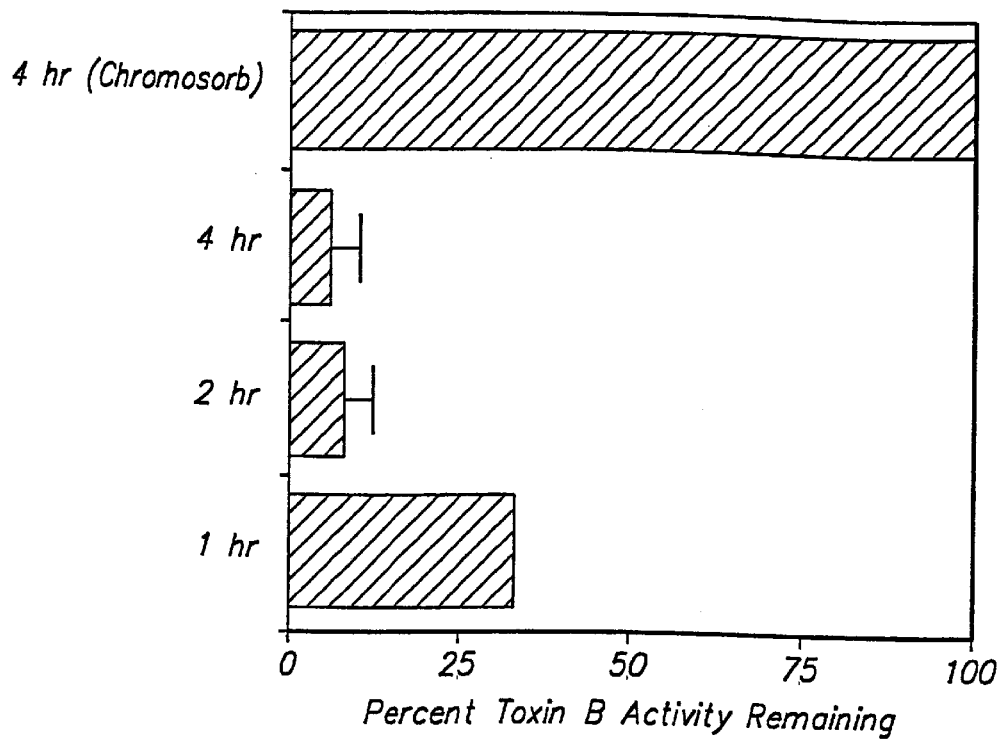
FIGS. 1A and B illustrate the time and concentration dependent neutralization of C. difficile toxin B activity using SYNSORB 5-128.

As used herein the following terms have the following meanings:

The term "antibiotic-associated bacterial diarrhea" refers to the condition wherein antibiotic therapy disturbs the balance of the microbial flora of the gut, allowing pathogenic organisms such as Clostridium difficile to flourish. These organisms cause diarrhea. Antibiotic-associated bacterial diarrhea includes such conditions as Clostridium difficile associated diarrhea (CDAD) and pseudomembranous colitis (PMC).

The term "biocompatible" refers to chemical inertness with respect to human tissues or body fluids.

The terms "compatible linker arm" or "linker arm" refer to a moiety which serves to space the oligosaccharide structure from the biocompatible support and which is bifunctional wherein one functional group is capable of binding to a reciprocal functional group of the support and the other functional group is capable of binding to a reciprocal functional group of the oligosaccharide structure.

Compatible linker arms preferred in the present invention are non-peptidyl spacer arms. The oligosaccharide may be linked via an 8-methoxycarbonyloctyl linker or via another appropriate non-peptidyl linker, such as a urea-like linker arm of the formula —NH—$(CH_2)_m$—NHC(O)NH—, where m is an integer of from about 2 to about 10.

The term "oligosaccharide" means saccharides comprising 1 to about 20 saccharide moieties. Saccharide derivatives may also be used as saccharide moieties included in the term oligosaccharide [67–69].

The term "pseudomembranous colitis" (PMC), also known as pseudomembranous enterocolitis or enteritis, refers to the inflammation of the mucous membrane of both small and large intestine with the formation and passage of pseudomembranous material (composed of fibrin, mucous, necrotic epithelial cells and leukocytes) in the stools.

The term "support" refers to an inert material to which the oligosaccharide sequences may be bound or immobilized via a compatible linker arm. Where use is in vivo, the support will be biocompatible.

The term "SYNSORB" refers to 8-methoxycarbonyloctyl oligosaccharide structures covalently coupled to Chromosorb P™(Manville Corp., Denver, Colo.) [12], a derivatized silica particle material. Where indicated, the SYNSORB may use a urea-like linker arm rather than the 8-methoxycarbonyloctyl linker.

The term "toxin A" refers to an enterotoxin of Clostridium difficile which initiates CDAD and related conditions. This toxin has a lectin-like activity.

The term "toxin B" refers to a cytotoxin of Clostridium difficile which causes destruction of intestinal cells and induces the release of inflammatory mediators.

For purpose of this application, all sugars are referenced using conventional three letter nomenclature. All sugars are assumed to be in the D-form unless otherwise noted, except for fucose, which is in the L-form. Further all sugars are in the pyranose form.

B. Pharmacology

Amino acid sequences in C. difficile toxin A and B that are similar to sequences responsible for oligosaccharide binding in Streptococcal glucan binding proteins have been reported [49–51]. Although, as noted above, the receptor for toxin B is not known, the oligosaccharide binding specificity for these glucan binding proteins is for repeated glucose units linked together as shown below [52]:

$$\alpha Glc(1\rightarrow 6)\alpha Glc(1\rightarrow 6)\alpha Glc \ldots$$

Figure 1B:
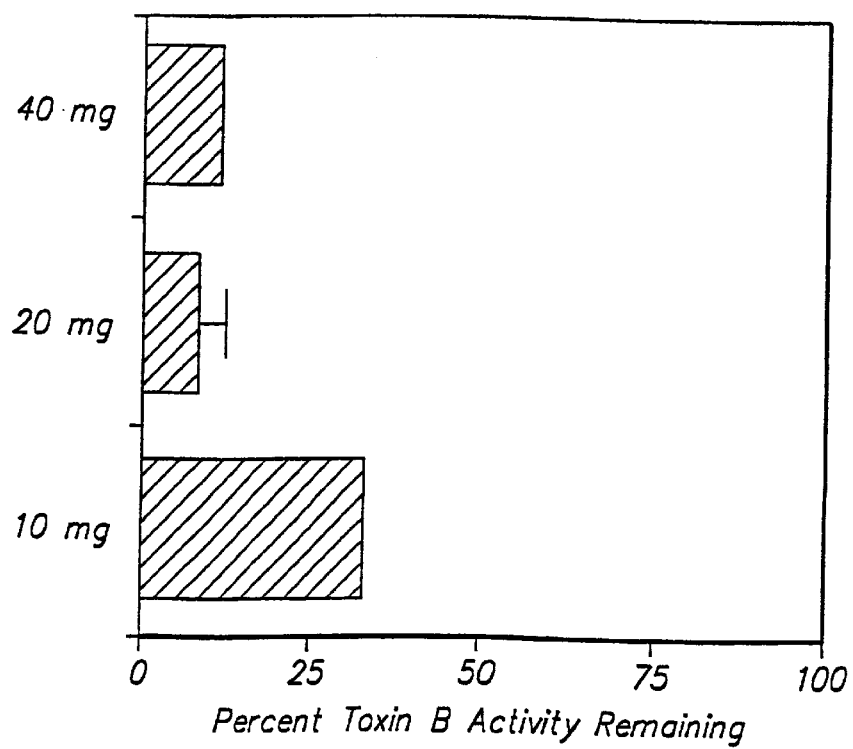

The oligosaccharide isomaltotriose ($\alpha Glc(1-6)\alpha Glc(1-6)$ Glc) was immobilized by attachment onto Chromosorb P using a linker arm, and tested in toxin B neutralization experiments. The results from these experiments are presented graphically in FIGS. 1A and 1B, where concentration and time dependent neutralization of C. difficile toxin B cytotoxic activity using immobilized isomaltotriose SYNSORB (n=3) is shown. Concentration neutralization experiments were performed by incubating immobilized isomaltotriose (10, 20 or 40 mg) with 1 mL of toxin B for 2 hours at room temperature. The amount of toxin activity in each sample was measured using Chinese hamster ovary (CHO) cells.

The results are presented as the percent activity remaining relative to control toxin solutions that had not been incubated with SYNSORB. Time dependent neutralization experiments were performed by incubating toxin B with 20 mg samples of immobilized isomaltotriose SYNSORB for 1, 2 and 4 h at room temperature. A control incubation (4 h) of toxin B with Chromosorb P was included to determine the extent of background binding to the support. The results are presented as the percent activity remaining relative to control toxin solutions that had not been incubated with SYNSORB and indicate that toxin B bound to isomaltotriose SYNSORB in a concentration and time dependent manner. The results also indicated that toxin B binds to the support slowly, requiring up to 4 hours to achieve significant toxin B binding under these conditions. Further, these data show that oligosaccharides which contain a(1–6)-linked repeating units of glucose are effective at binding toxin B and can serve as a therapeutic for *C. difficile*-mediated diarrhea.

SYNSORBs which incorporate oligosaccharides terminating in glucose or N-acetylglucosamine were also examined for toxin B binding by measuring the cytotoxic activity of toxin B with or without SYNSORB in CHO cells. Results of these studies are shown in Table 1, where * indicates SYNSORBs using the urea-like linker arm.

TABLE 1

Toxin B Neutralization Studies

| SYNSORB Number | Common Name | Oligosaccharide Structure | Percent Neutralization | Percent Neutralization in Presence of 0.5% BSA |
|---|---|---|---|---|
| 23 | — | βGlc | 0 | 0 |
| 38 | — | αGlc(1-2)βGal | 78 ± 16 | 80 |
| 3-74* | maltose | αGlc(1-4)βGlc | 96 ± 0 | 80 |
| 3-76* | cellobiose | βGlc(1-4)βGlc | 93 ± 5 | 80 |
| 5-128* | isomaltotriose | αGlc(1-6)αGlc(1-6)βGlc | 96 ± 0 | 80 |
| 179A* | isomaltose | αGlc(1-6)βGlc | 96 ± 9 | N.D. |
| 78 | chitobiose | βGlcNAc(1-4)βGlcNAc | 93 ± 5 | 80 |

All SYNSORBS tested except SYNSORB 23 effectively neutralized toxin B cytotoxicity. By comparison, toxin A did not bind to the SYNSORBs 5-128 (isomaltotriose) and 179A (isomaltose). The other SYNSORBs in Table 1 were not tested against toxin A. This observation confirms that there are differences in the binding specificity of toxin A and toxin B, even though there is some amino acid homology (60% amino acid homology) between the two toxins. Oligosaccharides which bind toxin A have been identified [65–66].

We also utilized a SYNSORB derivative that incorporates two different oligosaccharide ligands. The ligands selected for the dual labelling of Chromosorb P™ were based on previous results which revealed differential oligosaccharide binding specificities for toxins A and B. Since the oligosaccharide αGal(1–3)βGal(1–4)βGlc (Cd) binds toxin A but not toxin B, it was selected for use as the toxin A neutralizing component, and was immobilized onto amino derivatized Chromosorb P using an 8-methoxycarbonyl octyl linker arm. Toxin B but not toxin A binds to isomaltose (αGlc(1–6)Glc). Utilizing the amino derivatized Chromosorb that already incorporated the Cd oligosaccharide, isomaltose was immobilized onto the support using the recently developed "Instasorb" linker arm technology as disclosed in PCT/CA97/00851 [70]. The resulting SYNSORB (SYNSORB 5174, which has both oligosaccharides covalently bound by their respective linkers) was then tested for toxin A and B binding. SYNSORB Cd and isomaltose SYNSORB (SYNSORB 179A) were included as controls. The results, presented in FIG. 3, show that SYNSORB 5174 neutralized both toxin A and B activity. The results also indicate the toxin neutralizing capacity of SYNSORB 5174 was comparable to SYNSORB Cd and SYNSORB 179A. Thus, a support comprising more than one oligosaccharide ligand can be used to bind both toxin A and toxin B.

C. Synthesis

Chemical methods for the synthesis of oligosaccharide structures can be accomplished by methods known in the art. These materials are generally assembled using suitably protected individual monosaccharides.

The specific methods employed are generally adapted and optimized for each individual structure to be synthesized. In general, the chemical synthesis of all or part of the oligosaccharide glycosides first involves formation of a glycosidic linkage on the anomeric carbon atom of the reducing sugar or monosaccharide. Specifically, an appropriately protected form of a naturally occurring or of a chemically modified saccharide structure (the glycosyl donor) is selectively modified at the anomeric center of the reducing unit so as to introduce a leaving group comprising halides, trichloroacetimidate, acetyl, thioglycoside, etc. The donor is then reacted under catalytic conditions well known in the art with an aglycon or an appropriate form of a carbohydrate acceptor which possesses one free hydroxyl group at the position where the glycosidic linkage is to be established.

A large variety of aglycon moieties are known in the art and can be attached with the proper configuration to the anomeric center of the reducing unit. Appropriate use of compatible blocking groups, well known in the art of carbohydrate synthesis, will allow selective modification of the synthesized structures or the further attachment of additional sugar units or sugar blocks to the acceptor structures.

After formation of the glycosidic linkage, the saccharide glycoside can be used to effect coupling of additional saccharide unit(s) or chemically modified at selected positions or, after conventional deprotection, used in an enzymatic synthesis. In general, chemical coupling of a naturally occurring or chemically modified saccharide unit to the saccharide glycoside is accomplished by employing established chemistry well documented in the literature [21–37].

The supports to which the oligosaccharide structures of the present invention are bound or immobilized include a wide variety of biocompatible materials known in the art. Water soluble biocompatible polymers such as hydrogels, carboxymethyl celluloses, synthetic polymers, and the like are particularly preferred. In particular, these supports are useful for delivery to the gut, especially prolonged delivery. Useful supports are non-absorbable, that is to say that they may be soluble or insoluble, so long as they are not absorbed by the body.

Solid supports are particularly useful for certain applications. Such solid supports to which the oligosaccharide structures of the present invention are bound may be in the form of sheets or particles. A large variety of biocompatible solid support materials are known in the art. Examples thereof are silica, synthetic silicates such as porous glass, biogenic silicates such as diatomaceous earth, silicate-containing minerals such as kaolinite, and synthetic polymers such as polystyrene, polypropylene, and polysaccharides. Preferably the solid supports have a particle size of from about 10 to 500 microns for in vivo use. In particular, particle sizes of 100 to 200 microns are preferred.

The oligosaccharide structure(s) is covalently bound or noncovalently (passively) adsorbed onto the support so as to be immobilized. The covalent bonding may be via reaction between functional groups on the support and the compatible linker arm of the oligosaccharide structure. It has unexpectedly been found that attachment of the oligosaccharide structure to the biocompatible support through a compatible linking arm provides a product which, notwithstanding the support, effectively removes toxin. Linking moieties that are used in indirect bonding are preferably organic bifunctional molecules of appropriate length (at least one carbon atom) which serve simply to distance the oligosaccharide structure from the surface of the support.

The compositions of this invention are preferably represented by the formula:

(OLIGOSACCHARIDE—Y—R)$_n$—SUPPORT where OLIGOSACCHARIDE represents an oligosaccharide group of at least 1 sugar unit which group binds to toxin B or toxins A and B, Y is oxygen, sulfur or nitrogen, R is an aglycon linking arm of at least 1 carbon atom, SUPPORT is as defined above, and n is an integer greater than or equal to 1. Oligosaccharide sequences containing about 2 to 10 saccharide units may be used. Sequences with about 2 to 4 saccharide units are preferred. In some instances, more than one oligosaccharide group may be linked to the support, e.g., one oligosaccharide group which binds toxin B and another which binds toxin A, to provide a composition which binds to more than one toxin moiety.

Numerous aglycon linking arms are known in the art. For example, a linking arm comprising a para-nitrophenyl group (i.e., —OC$_6$H$_4$pNO$_2$) has been disclosed [38]. At the appropriate time during synthesis, the nitro group is reduced to an amino group which can be protected as N-trifluoroacetamido. Prior to coupling to a support, the trifluoroacetamido group is removed thereby unmasking the amino group.

A linking arm containing sulfur has been disclosed [39]. Specifically, the linking arm is derived from a 2-bromoethyl group which, in a substitution reaction with thionucleophiles, has been shown to lead to linking arms possessing a variety of terminal functional groups such as, —OCH$_2$CH$_2$SCH$_2$CO$_2$CH$_3$ and —OCH$_2$CH$_2$SC$_6$H4—pNH$_2$. These terminal functional groups permit reaction to complementary functional groups on the support, thereby forming a covalent linkage to the support. Such reactions are well known in the art.

A 6-trifluoroacetamido-hexyl linking arm, (—O—(CH$_2$)$_6$—NHCOCF$_3$) has been disclosed [40] in which the trifluoroacetamido protecting group can be removed, unmasking the primary amino group used for coupling.

Other exemplifications of known linking arms include the 7-methoxycarbonyl-3,6,dioxaheptyl linking arm [41] (—OCH$_2$—CH$_2$)$_2$OCH$_2$CO$_2$CH$_3$); the 2-(4-methoxycarbonylbutan-carboxamido) ethyl [42] (—OCH$_2$CH$_2$NHC(O)(CH$_2$)$_4$CO$_2$CH$_3$); the allyl linking arm [43] (—OCH$_2$CH=CH$_2$) which, by radical co-polymerization with an appropriate monomer, leads to co-polymers; other allyl linking arms [44] are known (—O (CH$_2$CH$_2$O)$_2$CH$_2$CH=CH$_2$). Additionally, allyl linking arms can be derivatized in the presence of 2-aminoethanethiol [45] to provide for a linking arm —OCH$_2$CH$_2$CH$_2$SCH$_2$CH$_2$NH$_2$. Other suitable linking arms have also been disclosed [21–23, 25, 26]. The particular linking employed to covalently attach the oligosaccharide group to the support is not critical.

Preferably, the aglycon linking arm is a hydrophobic group and most preferably, the aglycon linking arm is a hydrophobic group selected from the group consisting of $$—(CH_2)_8\overset{O}{\overset{\|}{C}}—,$$

—(CH$_2$)$_5$OCH$_2$CH$_2$CH$_2$—, —(CH$_2$)$_8$CH$_2$O— and —NH—(CH$_2$)$_m$—NHC(O)NH—, where m is an integer of from about 2 to about 10.

$$—R^1—X—\overset{W}{\overset{\|}{C}}—Y(R^2X')_pR^2NR^3—,$$

Where R$^1$ is selected from the group consisting of a covalent bond and a divalent hydrocarbylene group having from 1 to about 20 carbon atoms; R$^2$ is a divalent hydrocarbylene group of from 2 to about 20 carbon atoms; each X' is independently selected from the group consisting of —O— and >NR$^4$ wherein each R$^4$ is independently selected from hydrogen, —R$^2$NH, or —R$^2$NR$^3$Z wherein R$^2$ is as defined above; R$^3$ is selected from the group consisting of hydrogen and —C(O)R$^5$ wherein R$^5$ is hydrocarbyl of from 1 to about 20 carbon atoms; W is selected from O or S; X is selected from the group consisting of —NH—, —O— and —S—; Y is selected from the group consisting of —NH—, —O— and —S—; and p is an integer from 0 to 50 or more, wherein the total number of atoms separating the support from the toxin-binding oligosaccharide is at least 8.

We have found that synthetic oligosaccharide sequences covalently attached to a biocompatible support, e.g., Chromosorb P™ (SYNSORB) may be used to bind toxin B. These compositions are useful to treat or prevent CDAD, PMC and other conditions associated with *C. difficile* infection. When a solid support is to be used, SYNSORB is particularly preferred for these compositions because it is non-toxic and resistant to mechanical and chemical degradation.

In studies using rats (a widely accepted model for pre-clinical studies, since they are predictive of human response), SYNSORBs have been found to pass unaffected through the rat gastrointestinal tract. They were found to be eliminated completely and rapidly (99% eliminated in 72 hours) following oral administration. Additionally, the high density of oligosaccharide moieties on SYNSORBs is particularly useful for binding toxins which have carbohydrate binding affinity. For example, toxin A is thought to possess multiple oligosaccharide binding sites [11].

Non-peptidyl linking arms are preferred for use as the compatible linking arms of the present invention. The use of glycopeptides is not desirable because glycopeptides contain several, often different, oligosaccharides linked to the same protein. Glycopeptides are also difficult to obtain in large amounts and require expensive and tedious purification. Likewise, the use of BSA or HSA conjugates is not desirable due to questionable stability in the gastrointestinal tract when given orally.

Covalent attachment of an oligosaccharide group containing a toxin B binding unit through a non-peptidyl spacer arm to an inert support permits efficient binding and removal of toxin B or toxins A and B from a sample to be analyzed for the presence of toxin B (or toxins A and B) or from the intestine of a patient suffering from or susceptible to CDAD, PMIIC or another condition associated with *C. difficile* infection. When the oligosaccharide is synthesized with this compatible linker arm attached (in non-derivatized form), highly pure compositions may be achieved which can be coupled to various supports.

D. Pharmaceutical Compositions

The methods of this invention are achieved by using pharmaceutical compositions comprising one or more oligosaccharide structures which bind toxin B attached to a support.

When used for oral administration, which is preferred, these compositions may be formulated in a variety of ways. It will preferably be in liquid or semisolid form. Compositions including a liquid pharmaceutically inert carrier such as water may be considered for oral administration. Other pharmaceutically compatible liquids or semisolids, may also be used. The use of such liquids and semisolids is well known to those of skill in the art. (See, e.g., Remington's Pharmaceutical Sciences, 18th edition, 1990.)

Compositions which may be mixed with liquid or semisolid foods such as enteral nutritional formulas, applesauce, ice cream or pudding may also be preferred. Formulations, such as SYNSORBs, which do not have a disagreeable taste or aftertaste are preferred. A nasogastric tube may also be used to deliver the compositions directly into the stomach.

Solid compositions may also be used, and may optionally and conveniently be used in formulations containing a pharmaceutically inert carrier, including conventional solid carriers such as lactose, starch, dextrin or magnesium stearate, which are conveniently presented in tablet or capsule form. The $(OLIGOSACCHARIDE-Y-R)_n-SUPPORT$ composition itself may also be used without the addition of inert pharmaceutical carriers, particularly for use in capsule form.

Doses are selected to provide neutralization and elimination of toxin B found in the gut of effected or at risk subjects. Useful doses are from about 0.25 to 1.25 micromoles of oligosaccharide/kg body weight/day, preferably about 0.5 to 1.0 micromoles of oligosaccharide/kg body weight/day. Using SYNSORB compositions, this means about 0.5 to 1.0 gram SYNSORB/kg body weight/day, which gives a concentration of SYNSORB in the gut of about 20 mg/ml. For subjects with clinical symptoms, administration is expected to be 3 or 4 times daily, for a period of one week or until clinical symptoms are resolved. For at risk subjects, prolonged prophylactic administration, e.g., in enteral nutritional formulas, is indicated. The dose level and schedule of administration may vary depending on the particular oligosaccharide structure used and such factors as the age and condition of the subject.

As discussed previously, oral administration is preferred, but formulations may also be considered for other means of administration such as per rectum. The usefulness of these formulations may depend on the particular composition used and the particular subject receiving the treatment. These formulations may contain a liquid carrier that may be oily, aqueous, emulsified or contain certain solvents suitable to the mode of administration.

Compositions may be formulated in unit dose form, or in multiple or subunit doses. For the expected doses set forth previously, orally administered liquid compositions should preferably contain about 1 micromole oligosaccharide/ml.

E. Methodology

We have found that *C. difficile* toxin B may be neutralized by certain oligosaccharide sequences which bind the toxin. In particular, synthetic oligosaccharides covalently attached to supports via non-peptidyl compatible linker arms have been found to neutralize toxin B or toxins A and B effectively. Examples of such compositions are certain SYNSORBs, which neutralize the activity of toxin B or toxins A and B.

We have tested the ability of several oligosaccharide sequences attached to Chromosorb P via 8-methoxylcarbonyloctyl (MCO) or urea-like spacer arms to neutralize toxin B or toxins A and B. The oligosaccharide sequences attached to supports useful in the present invention are those which bind toxin B and, in some cases, both toxins A and B.

The binding affinity of an oligosaccharide to toxin B is readily detectable by a simple in vitro test, as for example, set forth in Example 3 below. For the purposes of this invention, oligosaccharide sequences attached to supports which bind toxin B means those compositions which reduce cytotoxicity in CHO cell assays by at least 50%.

Several different oligosaccharide sequences attached to supports via compatible arms have been found to have the ability to neutralize toxin B (and in some cases, toxin A and B) activity. These sequences, and others that also bind toxin B, may be used to treat or prevent CDAD, PMC and other conditions associated with *C. difficile* infection. The optimal time for complete removal of toxin B activity was found to be about 4 hours at 37° C., using a concentration of SYNSORB of 20 mg in 1 ml sample. Since each gram of SYNSORB contains approximately 0.25 to 1.0 micromoles oligosaccharide, the total amount of oligosaccharide to be given in a daily dose would range from 7.5 to 30 micromoles, using a gut volume of four liters.

Treatment or prevention of CDAD, PMC or other conditions associated with *C. difficile* infection may be accomplished by oral administration of compositions containing oligosaccharide sequences covalently bound to a support via a compatible linker arm (e.g., SYNSORBs). For example, SYNSORBs have been found to pass through the stomach of rats intact. This means that they are intact when they contact toxin B in the intestinal tract. Subsequent elimination of intact SYNSORB with toxin B bound to it results in elimination of toxin B from the patient.

Oligosaccharide sequences covalently attached via compatible linker arms to a support, e.g., SYNSORBs, are useful to treat individuals who suffer from multiple episodes of diarrhea. Upon initial reoccurrence of diarrhea, patients would be treated with SYNSORB to remove toxin B or both toxin A and toxin B from the intestine. The removal of toxin A prevents the initial tissue damage to the intestinal lining, which leads to prevention or reduction of diarrhea. Removal of toxin B prevents the cytotoxicity of this toxin to the intestinal and colonic cells, which also leads to prevention or reduction of diarrhea. No further treatment with antibiotics need be given, allowing the re-establishment of the normal intestinal microflora within the gut. The advantage of such treatment is that it does not affect the recolonization of the intestinal tract by normal microflora. Treatment until discontinuance of diarrhea would allow complete recovery.

In addition to its usefulness in patients suffering from recurring diarrhea, treatment with oligosaccharide sequences covalently attached via compatible linker arms to supports, e.g., SYNSORBs, may be used to treat all individuals who suffer from or are prone to develop CDAD, PMC or other conditions associated with *C. difficile* infection. The use of the oligosaccharide-support compositions of the present invention in combination with antibiotic therapy will be able to reduce the diarrhea more effectively, leading to more rapid recovery.

Toxin B and/or toxin A may be measured directly on the surface of the oligosaccharide-containing support using any suitable detection system. For example, radioactive, biotinylated or fluorescently labelled monoclonal or polyclonal antibodies specific for the toxin may be used to determine the amount of toxin bound to the support. A wide variety of protocols for detection of formation of specific binding complexes analogous to standard immunoassay techniques is well known in the art.

EXAMPLES

The following methods were used to perform the studies in the Examples that follow. Terms and abbreviations are consistent with those in current use in this art.

1. Toxin Purification

Toxins A and B were isolated from a toxin producing strain of *C. difficile* (ATCC 43255, VPI strain 10463) using slight modifications of the method of Sullivan et al. as described previously [2,21]. The toxin B fraction was devoid of toxin A activity, as determined by the inability of the toxin containing solution to hemagglutinate rabbit erythrocytes.

2. Toxin A Hemagglutination Assays Using Rabbit Erythrocytes

Fresh rabbit erythrocytes were washed once in Tris buffered saline (TBS, pH 7.4) and resuspended at a concentration of 4% (vol/vol) in TBS. Serial two-fold dilutions (50 μL) of toxin A solutions were made in TBS in U-shaped microtitre wells. An equal volume (50 μL) of rabbit erythrocytes was then added to each well and the microtitre plate was mixed gently. Toxin A hemagglutination assays were incubated at 4° C. for 4 h. The hemagglutination titre was then assessed visually. All assays were done in duplicate.

3. Assay of Toxin B Activity Using Chinese Hamster Ovary Cells

Chinese hamster ovary (CHO) cells were maintained in Hams F12 media supplemented with 10% fetal bovine serum in an atmosphere of 5% $CO_2$ at 37° C. Samples to be tested for toxin B activity were diluted 1:10 in Hams media and filter sterilized through 0.22 micron syringe filters. Samples were serial 3-fold diluted in media and 1 00 μL of each dilution was added to wells with confluent monolayers of CHO cells and incubated for 24 h at 37° C. / 5%$CO_2$.

Each sample was analyzed two times. Cytotoxic effects were recorded after 24 h incubation by comparing test sample wells with control wells that did not contain toxin B. After 24 h, the cells were fixed with 95% methanol and stained with Geimsa stain. Samples from neutralization experiments were treated in an analogous fashion. The percent neutralization was determined by comparing the end point dilutions of samples with and without SYNSORB treatment.

4. Toxin A and B Neutralization Assays

PBS solutions with or without 0.5% BSA containing purified toxin B and/or A (0.5 mL) were added to SYNSORBs (10 mg) in 0.5 mL microcentrifuge tubes and incubated at room temperature for 1 h on an end-over-end rotator. After incubation, the SYNSORB was allowed to settle to the bottom of the tubes and the supernatants were carefully removed. Serial two-fold dilutions of the supernatants were prepared in Tris buffered saline (TBS) and the end point titers in the hemagglutination or CHO cell assays was determined as described above. The percent binding of either toxin B and/or toxin A was calculated relative to the end-point titers of toxin solutions incubated with no SYNSORB or with Chromosorb P containing only the non-peptidyl linker arm.

Example 1

Determining Conditions for Toxin B Binding to Isomaltotriose SYNSORB

The conditions required for toxin B binding were determined by incubating 20 mg samples of isomaltotriose SYNSORB (5–128) or Chromosorb with 1 mL of a purified toxin B solution in 1.5 mL microcentrifuge tubes for 1, 2 and 4 h at room temperature on an end-over-end rotator. Control tubes containing toxin B solution but no SYNSORB or Chromosorb were incubated at the same time. Determination of the optimal amount of isomaltotriose SYNSORB required for maximum toxin B neutralization was performed by incubating immobilized isomaltotriose (10, 20 or 40 mg) with 1 mL of toxin B for 2 hours at room temperature. The amount of toxin activity in each sample was measured using CHO cells. After incubation, the SYNSORB was allowed to settle to the bottom of the tubes and the supernatants were carefully removed. Serial five-fold dilutions of the supernatants were prepared and the cytotoxic end point determined as described above. Each experiment was done in at least duplicate. The extent of reduction in the end point in the presence of SYNSORB was determined by comparing with controls in which SYNSORB was not added. The results of these experiments are presented in FIGS. 1A and 1B, and show that SYNSORB 5174 was effective to neutralize toxin B activity.

Example 2

Screening of Oligosaccharides for Toxin B Neutralization

Solutions containing purified toxin B (1 mL) were added to various SYNSORBs listed in Table 1 (20 mg) containing different oligosaccharide sequences in 1.5 mL microcentrifuge tubes and incubated at room temperature for 4 h on an end-over-end rotator. The amount of neutralization in each sample was determined by comparing the cytotoxic end point titres of CHO cell assays from samples with and without SYNSORB.

As shown in Table 1, all of the oligosaccharides tested except βGlc effectively neutralized toxin B cytotoxicity. Thus, the oligosaccharides αGlc(1–2)βGal, αGlc(1–4)βGlc (maltose), βGlc(1–4)βGlc(cellobiose), αGlc(1–6)αGlc (1–6)αGlc (isomaltotriose), αGlc(1≠6)αGlc (isomaltose) and βGlcNAc(1–4)βGlcNAc (chitobiose) bound toxin B.

Example 3

Toxin A Neutralization Assays Using Isomaltose and Isomaltotriose SYNSORBs

Solutions containing purified toxin A (0.5 mL) were added to isomaltose or isomaltotriose SYNSORBs (10 or 20 mg) in 0.5 mL microcentrifuge tubes and incubated at either 4° C. or room temperature for 1 h on an end-over-end rotator. After incubation, the SYNSORB was allowed to settle to the bottom of the tubes and the supernatants were carefully removed. Serial two-fold dilutions of the supernatants were prepared in Tris buffered saline (TBS) and the hemagglutination end point determined as described above. The extent of reduction in the end point in the presence of either SYNSORB was determined by comparing with controls in which SYNSORB was not added. We did not detect any toxin A binding to either isomaltose or isomaltotriose SYNSORB, indicating that toxin A has different binding specificity from toxin B.

Example 4

Neutralization of Both Toxin A and Toxin B

Neutralization experiments of *C. difficile* toxin A hemagglutinating and toxin B cytotoxic activity were performed using a "dual-labelled" SYNSORB, i.e., SYNSORB 5174 which has both the Cd oligosaccharide (αGal(1–3)βGal(1–4)βGlc) and isomaltose, each attached by its respective linker (n=2). Neutralization experiments were done by incubating either SYNSORB 5174, 179A (isomaltose) or Cd at a concentration of 20 mgl mL with toxin A for 1 h or toxin B for 4 hours at room temperature. The amount of toxin activity in each sample was measured using CHO cells or rabbit erythrocytes. The results are presented as the percent activity remaining relative to control toxin solutions that had not been incubated with SYNSORB.

The results, presented in FIG. 2, show that SYNSORB 5174 neutralized both toxin A and B activity. The results also indicate the toxin neutralizing capacity of SYNSORB 5174 was comparable to SYNSORB Cd and SYNSORB 179A. Thus, a support comprising more than one oligosaccharide ligand can be used to bind both toxin A and toxin B.

What is claimed is:

1. A pharmaceutical composition useful to bind *C. difficile* toxin B in a subject, which composition comprises:
   a) at least one oligosaccharide sequence covalently attached to a pharmaceutically acceptable inert support through a non-peptidyl compatible linker arm, wherein said oligosaccharide sequence binds toxin B; and
   b) a pharmaceutically acceptable carrier, wherein said composition is capable of being eliminated from the gastrointestinal tract, and wherein said oligosaccharide sequence is αGlc(1–6)αGlc(1–6)βGlc and said linker arm is —NH—(CH$_2$)$_m$—NHC(O)NH—, where m is an integer of from about 2 to about 10.

2. A pharmaceutical composition useful to bind *C. difficile* toxin B in a subject, which composition comprises:
   a) at least one oligosaccharide sequence covalently attached to a pharmaceutically acceptable inert support tough a non-peptidyl compatible linker arm, wherein said oligosaccharide sequence binds toxin B; and
   b) a pharmaceutically acceptable carrier, wherein said composition is capable of being eliminated from the gastrointestinal tract, and wherein said oligosaccharide sequence is αGlc(1–6)βGlc and said linker arm is —NH—(CH$_2$)$_m$—NHC(O)NH—, where m is an integer of from about 2 to about 10.

3. A method to bind toxin B in a subject, which method comprises administering to said subject a composition comprising the oligosaccharide sequence αGlc(1–6)αGlc(1–6)βGlc covalently attached to a pharmaceutically acceptable inert support through a linker arm which is —NH—(CH$_2$)$_m$—NHC(O)NH—, where m is an integer of from about 2 to about 10, wherein said composition contacts and binds toxin B, and wherein said composition is capable of being eliminated from the gastrointestinal tract.

4. A method to bind toxin B in a subject, which method comprises administering to said subject a composition comprising the oligosaccharide sequence αGlc(1–6)βGlc covalently attached to a pharmaceutically acceptable inert support through a linker arm which is —NH—(CH$_2$)$_m$—NHC(O)NH—, where m is an integer of from about 2 to about 10, wherein said composition contacts and binds toxin B, and wherein said composition is capable of being eliminated from the gastrointestinal tract.

5. A pharmaceutical composition useful to bind *C. difficile* toxin B in a subject, which composition comprises:
   a) at least one oligosaccharide sequence covalently attached to a pharmaceutically acceptable inert support through a non-peptidyl compatible linker arm, wherein said oligosaccharide sequence binds toxin B; and
   b) a pharmaceutically acceptable carrier,
   wherein said composition is capable of being eliminated from the gastrointestinal tract, and
   wherein said oligosaccharide sequence is αGlc(1–6)αGlc(1–6)βGlc and said linker arm is $$—R^1—X—\overset{\overset{W}{\|}}{C}—Y(R^2X')_pR^2NR^3—,$$

where R' is selected from the group consisting of a covalent bond and a divalent hydrocarbylene group having from 1 to about 20 carbon atoms; R$^2$ is a divalent hydrocarbylene group of from 2 to about 20 carbon atoms; each X' is independently selected from the group consisting of —O— and >NR$^4$ wherein each R$^4$ is independently selected from hydrogen, —R$^2$NH$_2$ or —R2NR$^3$Z wherein R$^2$ is as defined above; R$^3$ is selected from the group consisting of hydrogen and —C(O)R$^5$ wherein R$^5$ is hydrocarbyl of from 1 to about 20 carbon atoms; W is selected from O or S; X is selected from the group consisting of —NH—, —O— and —S—; Y is selected from the group consisting of —NH—, —O— and —S—; and p is an integer of from 0 to 50, wherein the total number of atoms separating the support from the toxin-binding oligosaccharide is at least 8.

6. A pharmaceutical composition useful to bind *C. difficile* toxin B in a subject, which composition comprises:
   a) at least one oligosaccharide sequence covalently attached to a pharmaceutically acceptable inert support through a non-peptidyl compatible linker arm, wherein said oligosaccharide sequence binds toxin B; and
   b) a pharmaceutically acceptable carrier,
   wherein said composition is capable of being eliminated from the gastrointestinal tract, and
   wherein said oligosaccharide sequence is αGlc(1–6)αGlc(1–6)βGlc and said linker arm is $$—R^1—X—\overset{\overset{W}{\|}}{C}—Y(R^2X')_pR^2NR^3—,$$

where R$^1$ is selected from the group consisting of a covalent bond and a divalent hydrocarbylene group having from 1 to about 20 carbon atoms; R$^2$ is a divalent hydrocarbylene group of from 2 to about 20 carbon atoms; each X' is independently selected from the group consisting of —O— and >NR$^4$ wherein each R$^4$ is independently selected from hydrogen, —R$^2$NH$_2$ or —R$^2$NR$^3$Z wherein R$^2$ is as defined above; R$^3$ is selected from the group consisting of hydrogen and —C(O)R$^5$ wherein R$^5$ is hydrocarbyl of from 1 to about 20 carbon atoms; W is selected from O or S; X is selected from the group consisting of —NH—, —O— and —S—; Y is selected from the group consisting of —NH—, —O—and —S—; and p is an integer of from 0 to 50, wherein the total number of atoms separating the support from the toxin-binding oligosaccharide is at least 8.

7. A method to bind toxin B in a subject, which method comprises administering to said subject a composition comprising the oligosaccharide sequence αGlc(1–6)αGlc(1–6)βGlc covalently attached to a pharmaceutically acceptable inert support through a linker arm which is αGlc(1–6)αGlc(1–6)βGlc and said linker arm is $$-R^1-X-\overset{\overset{W}{\|}}{C}-Y(R^2X')_pR^2NR^3-,$$

where $R^1$ is selected from the group consisting of a covalent bond and a divalent hydrocarbylene group having from 1 to about 20 carbon atoms; $R^2$ is a divalent hydrocarbylene group of from 2 to about 20 carbon atoms; each X' is independently selected from the group consisting of —O— and >$NR^4$ wherein each $R^4$ is independently selected from hydrogen, —$R_2NH_2$ or —$R^2NR^3Z$ wherein $R^2$ is as defined above; $R^3$ is selected from the group consisting of hydrogen and —$C(O)R^5$ wherein $R^5$ is hydrocarbyl of from 1 to about 20 carbon atoms; W is selected from O or S; X is selected from the group consisting of —NH—, —O— and —S—; Y is selected from the group consisting of —NH—, —O— and —S—; and p is an integer of from 0 to 50, wherein the total number of atoms separating the support from the toxin-binding oligosaccharide is at least 8, wherein said composition contacts and binds toxin B, and wherein said composition is capable of being eliminated from the gastrointestinal tract.

8. A method to bind toxin B in a subject, which method comprises administering to said subject a composition comprising the oligosaccharide sequence αGlc(1–6)βGlc covalently attached to a pharmaceutically acceptable inert support through a linker arm which is αGlc(1–6)αGlc(1–6)βGlc and said linker arm is $$-R^1-X-\overset{\overset{W}{\|}}{C}-Y(R^2X')_pR^2NR^3-,$$

where $R^1$ is selected from the group consisting of a covalent bond and a divalent hydrocarbylene group having from 1 to about 20 carbon atoms; $R^2$ is a divalent hydrocarbylene group of from 2 to about 20 carbon atoms; each X' is independently selected from the group consisting of —O— and >$NR^4$ wherein each $R^4$ is independently selected from hydrogen, —$R^2NH_2$ or —$R^2NR^3Z$ wherein $R^2$ is as defined above; $R^3$ is selected from the group consisting of hydrogen and —$C(O)R^5$ wherein $R^5$ is hydrocarbyl of from 1 to about 20 carbon atoms; W is selected from O or S; X is selected from the group consisting of —NH—, —O— and —S—; Y is selected from the group consisting of —NH—, —O— and —S—; and p is an integer of from 0 to 50, wherein the total number of atoms separating the support from the toxin-binding oligosaccharide is at least 8, wherein said composition contacts and binds toxin B, and wherein said composition is capable of being eliminated from the gastrointestinal tract.

* * * * *